(12) United States Patent
Peterson et al.

(10) Patent No.: US 9,615,787 B2
(45) Date of Patent: Apr. 11, 2017

(54) DETERMINING WHETHER TO CHANGE A TIME AT WHICH AN ALARM IS TO OCCUR BASED AT LEAST IN PART ON SLEEP DATA

(71) Applicant: Lenovo (Singapore) Pte. Ltd., New Tech Park (SG)

(72) Inventors: Nathan J. Peterson, Durham, NC (US); Russell Speight VanBlon, Raleigh, NC (US); Rod David Waltermann, Rougemont, NC (US); Arnold S. Weksler, Raleigh, NC (US); John Carl Mese, Cary, NC (US)

(73) Assignee: Lenovo (Singapre) Pte. Ltd., New Tech Park (SG)

(*) Notice: Subject to any disclaimer, the term of this patent is extended or adjusted under 35 U.S.C. 154(b) by 94 days.

(21) Appl. No.: 14/339,800

(22) Filed: Jul. 24, 2014

(65) Prior Publication Data

US 2016/0022202 A1 Jan. 28, 2016

(51) Int. Cl.
| | |
|---|---|
| *G04B 47/06* | (2006.01) |
| *G04G 13/02* | (2006.01) |
| *G04G 21/02* | (2010.01) |
| *A61B 5/00* | (2006.01) |
| *A61B 5/024* | (2006.01) |
| *A61B 5/0476* | (2006.01) |
| *A61B 5/08* | (2006.01) |
| *A61B 5/01* | (2006.01) |

(52) U.S. Cl.
CPC .......... *A61B 5/4812* (2013.01); *A61B 5/4815* (2013.01); *A61B 5/746* (2013.01); *G04B 47/063* (2013.01); *G04G 13/023* (2013.01); *G04G 13/026* (2013.01); *A61B 5/01* (2013.01); *A61B 5/024* (2013.01); *A61B 5/0476* (2013.01); *A61B 5/0816* (2013.01); *G04G 21/025* (2013.01)

(58) Field of Classification Search
CPC ... A61B 5/1118; A61B 5/4806; A61B 5/4809; A61B 5/4812; A61B 5/4815; A61B 5/01; A61B 5/024; A61B 5/0476; A61B 5/0816; A61B 5/746; G04B 47/00; G04B 47/063; G04G 13/023; G04G 13/026; G04G 21/025
USPC ............ 368/10, 11; 600/300, 534, 544, 595; 340/573.1, 575
See application file for complete search history.

(56) References Cited

U.S. PATENT DOCUMENTS

| | | | | |
|---|---|---|---|---|
| 3,871,169 A * | 3/1975 | Schwaar | ............... | G04B 27/005 368/195 |
| 4,228,806 A * | 10/1980 | Lidow | .................. | A61B 5/0476 368/12 |
| 6,928,031 B1 * | 8/2005 | Kanevsky | ............ | A61B 5/4812 368/10 |
| 2001/0048639 A1 * | 12/2001 | Davidson | ................ | G04F 1/005 368/82 |
| 2005/0012622 A1 * | 1/2005 | Sutton | ................... | A61M 21/00 340/573.1 |

(Continued)

*Primary Examiner* — Vit W Miska
(74) *Attorney, Agent, or Firm* — John L. Rogitz; John M. Rogitz

(57) ABSTRACT

In one aspect, a device includes a processor and a memory accessible to the processor. The memory bears instructions executable by the processor to receive data from a sleep sensor in communication with the device and, based at least in part on the data, determine whether to change a time at which an alarm is to occur at the device.

20 Claims, 6 Drawing Sheets

(56) References Cited

U.S. PATENT DOCUMENTS

| | | | |
|---|---|---|---|
| 2005/0190065 A1* | 9/2005 | Ronnholm | A61M 21/00 340/575 |
| 2006/0224047 A1* | 10/2006 | Suzuki | A61B 5/1118 600/300 |
| 2007/0287930 A1* | 12/2007 | Sutton | A61M 21/00 600/544 |
| 2008/0234785 A1* | 9/2008 | Nakayama | A61B 5/0205 607/62 |
| 2010/0170043 A1* | 7/2010 | Young | A47C 27/082 5/706 |
| 2011/0230790 A1* | 9/2011 | Kozlov | A61B 5/4812 600/595 |
| 2011/0291842 A1* | 12/2011 | Oexman | G08B 21/06 340/575 |
| 2012/0092171 A1* | 4/2012 | Hwang | G06F 19/345 340/575 |
| 2013/0018284 A1* | 1/2013 | Kahn | G04G 13/026 600/595 |
| 2013/0163394 A1* | 6/2013 | Loree, IV | G04G 11/00 368/256 |
| 2014/0210626 A1* | 7/2014 | Kresser | G08B 21/06 340/575 |
| 2014/0269223 A1* | 9/2014 | Mokhnatkina | G04G 13/02 368/73 |
| 2014/0269224 A1* | 9/2014 | Huh | G04G 13/021 368/73 |

* cited by examiner

| | Latest alarm time | amount of sleep desired | amount of REM sleep desired | sleep start time | sleep end time | amount of sleep received | amount of REM sleep received |
|---|---|---|---|---|---|---|---|
| Night 1 | 6:00 am | 8 hours | 4 hours | 9:00 pm | 5:30 am | 6 hours | 2 hours |
| Night 2 | 6:15 am | 8 hours | 4 hours | 9:30 pm | 6:15 am | 7.5 hours | 4 hours |
| Night 3 | 6:00 am | 8 hours | 4 hours | 9:15 pm | 5:52 am | 7.8 hours | 4 hours |

DETERMINING WHETHER TO CHANGE A TIME AT WHICH AN ALARM IS TO OCCUR BASED AT LEAST IN PART ON SLEEP DATA

FIELD

The present application relates generally to determining whether to change a time at which an alarm is to occur based at least in part on sleep data.

BACKGROUND

Today's alarms wake a person up at a specific time typically specified by the person. These alarms do not take into account things that may occur in the middle of the night that may deprive the person of some much-needed sleep, including e.g. sleep critical to a medical condition for which adequate sleep is needed, and thus such alarms wake the person up before adequate sleep is received. There are currently no adequate and/or cost effective solutions for remedying the foregoing.

SUMMARY

Accordingly, in one aspect a device includes a processor and a memory accessible to the processor. The memory bears instructions executable by the processor to receive data from a sleep sensor in communication with the device and, based at least in part on the data, determine whether to change a time at which an alarm is to occur at the device.

In another aspect, a method includes receiving input at an information handling system pertaining to an amount of sleep to receive prior to activating an alarm, receiving input at the information handling device pertaining to a threshold time at which the alarm is to be activated regardless of the amount of sleep, monitoring a user's sleep based on data from a sleep sensor, and determining whether at least one of the amount of sleep has been reached and the threshold time has been reached.

In still another aspect, a device includes a sleep sensor, a speaker, a processor, and a memory accessible to the processor. The memory bears instructions executable by the processor to monitor sleep of a person based on input from the sleep sensor and determine a time at which an alarm is to occur based at least in part on the input and based at least in part on at least one parameter input to the device by a user.

The details of present principles, both as to their structure and operation, can best be understood in reference to the accompanying drawings, in which like reference numerals refer to like parts, and in which:

DETAILED DESCRIPTION

Figure 1:
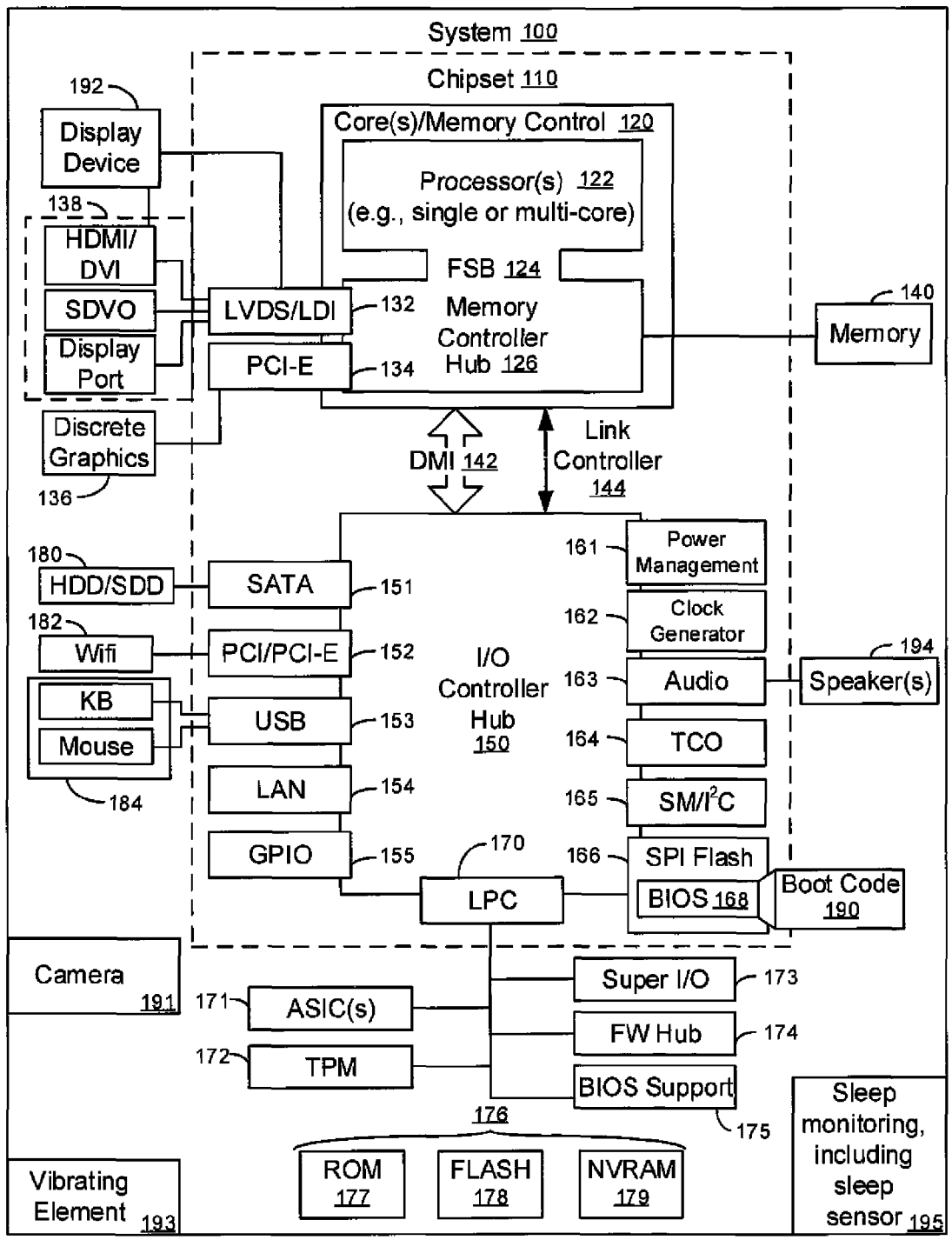
FIG. 1 is a block diagram of an example system in accordance with present principles.

This disclosure relates generally to device-based information. With respect to any computer systems discussed herein, a system may include server and client components, connected over a network such that data may be exchanged between the client and server components. The client components may include one or more computing devices including televisions (e.g. smart TVs, Internet-enabled TVs), computers such as desktops, laptops and tablet computers, so-called convertible devices (e.g. having a tablet configuration and laptop configuration), and other mobile devices including smart phones. These client devices may employ, as non-limiting examples, operating systems from Apple, Google, or Microsoft. A Unix or similar such as Linux operating system may be used. These operating systems can execute one or more browsers such as a browser made by Microsoft or Google or Mozilla or other browser program that can access web applications hosted by the Internet servers over a network such as the Internet, a local intranet, or a virtual private network.

As used herein, instructions refer to computer-implemented steps for processing information in the system. Instructions can be implemented in software, firmware or hardware; hence, illustrative components, blocks, modules, circuits, and steps are set forth in terms of their functionality.

A processor may be any conventional general purpose single- or multi-chip processor that can execute logic by means of various lines such as address lines, data lines, and control lines and registers and shift registers. Moreover, any logical blocks, modules, and circuits described herein can be implemented or performed, in addition to a general purpose processor, in or by a digital signal processor (DSP), a field programmable gate array (FPGA) or other programmable logic device such as an application specific integrated circuit (ASIC), discrete gate or transistor logic, discrete hardware components, or any combination thereof designed to perform the functions described herein. A processor can be implemented by a controller or state machine or a combination of computing devices.

Any software and/or applications described by way of flow charts and/or user interfaces herein can include various sub-routines, procedures, etc. It is to be understood that logic divulged as being executed by e.g. a module can be redistributed to other software modules and/or combined together in a single module and/or made available in a shareable library.

Logic when implemented in software, can be written in an appropriate language such as but not limited to C# or C++, and can be stored on or transmitted through a computer-readable storage medium (e.g. that may not be a carrier wave) such as a random access memory (RAM), read-only memory (ROM), electrically erasable programmable read-only memory (EEPROM), compact disk read-only memory (CD-ROM) or other optical disk storage such as digital versatile disc (DVD), magnetic disk storage or other magnetic storage devices including removable thumb drives, etc. A connection may establish a computer-readable medium. Such connections can include, as examples, hard-wired cables including fiber optics and coaxial wires and twisted pair wires. Such connections may include wireless communication connections including infrared and radio.

In an example, a processor can access information over its input lines from data storage, such as the computer readable storage medium, and/or the processor can access information wirelessly from an Internet server by activating a wireless transceiver to send and receive data. Data typically is converted from analog signals to digital by circuitry between the antenna and the registers of the processor when being received and from digital to analog when being transmitted. The processor then processes the data through its shift registers to output calculated data on output lines, for presentation of the calculated data on the device.

Components included in one embodiment can be used in other embodiments in any appropriate combination. For example, any of the various components described herein and/or depicted in the Figures may be combined, interchanged or excluded from other embodiments.

"A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together, etc.

"A system having one or more of A, B, and C" (likewise "a system having one or more of A, B, or C" and "a system having one or more of A, B, C") includes systems that have A alone, B alone, C alone, A and B together, A and C together, B and C together, and/or A, B, and C together, etc.

The term "circuit" or "circuitry" is used in the summary, description, and/or claims. As is well known in the art, the term "circuitry" includes all levels of available integration, e.g., from discrete logic circuits to the highest level of circuit integration such as VLSI, and includes programmable logic components programmed to perform the functions of an embodiment as well as general-purpose or special-purpose processors programmed with instructions to perform those functions.

Now specifically in reference to FIG. 1, it shows an example block diagram of an information handling system and/or computer system 100. Note that in some embodiments the system 100 may be a desktop computer system, such as one of the ThinkCentre® or ThinkPad® series of personal computers sold by Lenovo (US) Inc. of Morrisville, N.C., or a workstation computer, such as the ThinkStation®, which are sold by Lenovo (US) Inc. of Morrisville, N.C.; however, as apparent from the description herein, a client device, a server or other machine in accordance with present principles may include other features or only some of the features of the system 100. Also, the system 100 may be e.g. a game console such as XBOX® or Playstation®.

As shown in FIG. 1, the system 100 includes a so-called chipset 110. A chipset refers to a group of integrated circuits, or chips, that are designed to work together. Chipsets are usually marketed as a single product (e.g., consider chipsets marketed under the brands INTEL®, AMD®, etc.).

In the example of FIG. 1, the chipset 110 has a particular architecture, which may vary to some extent depending on brand or manufacturer. The architecture of the chipset 110 includes a core and memory control group 120 and an I/O controller hub 150 that exchange information (e.g., data, signals, commands, etc.) via, for example, a direct management interface or direct media interface (DMI) 142 or a link controller 144. In the example of FIG. 1, the DMI 142 is a chip-to-chip interface (sometimes referred to as being a link between a "northbridge" and a "southbridge").

The core and memory control group 120 include one or more processors 122 (e.g., single core or multi-core, etc.) and a memory controller hub 126 that exchange information via a front side bus (FSB) 124. As described herein, various components of the core and memory control group 120 may be integrated onto a single processor die, for example, to make a chip that supplants the conventional "northbridge" style architecture.

The memory controller hub 126 interfaces with memory 140. For example, the memory controller hub 126 may provide support for DDR SDRAM memory (e.g., DDR, DDR2, DDR3, etc.). In general, the memory 140 is a type of random-access memory (RAM). It is often referred to as "system memory."

The memory controller hub 126 further includes a low-voltage differential signaling interface (LVDS) 132. The LVDS 132 may be a so-called LVDS Display Interface (LDI) for support of a display device 192 (e.g., a CRT, a flat panel, a projector, a touch-enabled display, etc.). A block 138 includes some examples of technologies that may be supported via the LVDS interface 132 (e.g., serial digital video, HDMI/DVI, display port). The memory controller hub 126 also includes one or more PCI-express interfaces (PCI-E) 134, for example, for support of discrete graphics 136. Discrete graphics using a PCI-E interface has become an alternative approach to an accelerated graphics port (AGP). For example, the memory controller hub 126 may include a 16-lane (x16) PCI-E port for an external PCI-E-based graphics card (including e.g. one of more GPUs). An example system may include AGP or PCI-E for support of graphics.

The I/O hub controller 150 includes a variety of interfaces. The example of FIG. 1 includes a SATA interface 151, one or more PCI-E interfaces 152 (optionally one or more legacy PCI interfaces), one or more USB interfaces 153, a LAN interface 154 (more generally a network interface for communication over at least one network such as the Internet, a WAN, a LAN, etc. under direction of the processor(s) 122), a general purpose I/O interface (GPIO) 155, a low-pin count (LPC) interface 170, a power management interface 161, a clock generator interface 162, an audio interface 163 (e.g., for speakers 194 to output audio), a total cost of operation (TCO) interface 164, a system management bus interface (e.g., a multi-master serial computer bus interface) 165, and a serial peripheral flash memory/controller interface (SPI Flash) 166, which, in the example of FIG. 1, includes BIOS 168 and boot code 190. With respect to network connections, the I/O hub controller 150 may include integrated gigabit Ethernet controller lines multiplexed with a PCI-E interface port. Other network features may operate independent of a PCI-E interface.

The interfaces of the I/O hub controller 150 provide for communication with various devices, networks, etc. For example, the SATA interface 151 provides for reading, writing or reading and writing information on one or more drives 180 such as HDDs, SDDs or a combination thereof, but in any case the drives 180 are understood to be e.g. tangible computer readable storage mediums that may not be carrier waves. The I/O hub controller 150 may also include an advanced host controller interface (AHCI) to support one or more drives 180. The PCI-E interface 152 allows for wireless connections 182 to devices, networks, etc. The USB interface 153 provides for input devices 184 such as keyboards (KB), mice and various other devices (e.g., cameras, phones, storage, media players, etc.).

In the example of FIG. 1, the LPC interface 170 provides for use of one or more ASICs 171, a trusted platform module (TPM) 172, a super I/O 173, a firmware hub 174, BIOS support 175 as well as various types of memory 176 such as ROM 177, Flash 178, and non-volatile RAM (NVRAM) 179. With respect to the TPM 172, this module may be in the form of a chip that can be used to authenticate software and hardware devices. For example, a TPM may be capable of performing platform authentication and may be used to verify that a system seeking access is the expected system.

The system 100, upon power on, may be configured to execute boot code 190 for the BIOS 168, as stored within the SPI Flash 166, and thereafter processes data under the control of one or more operating systems and application software (e.g., stored in system memory 140). An operating system may be stored in any of a variety of locations and accessed, for example, according to instructions of the BIOS 168.

A camera 191 is also shown, which is in communication with and provides input to the processor 122. The camera 191 may be, e.g., a thermal imaging camera, a digital camera such as a webcam, and/or a camera integrated into the system 100 and controllable by the processor 122 to gather pictures/images and/or video. Regardless, it is to be understood that included in, in addition to, and/or in lieu of the camera 191 there may be an optical sensor included on the system 100 for e.g. sensing data related to the sleep of a person.

Still in reference to FIG. 1, the system 100 also includes a vibrating element 193 that may be and/or include e.g. a motor for moving an eccentric weight of the vibrating element to generate a vibration at the system 100, as well as a sleep monitor 195 for monitoring the sleep of a person. The sleep monitor 195 may e.g. include its own processor, memory, and instructions executable by the processor and stored on the memory for monitoring sleep of a user such as e.g. rapid eye movement (REM) sleep, amount of sleep, etc. Furthermore, the monitor 195 may include one or more sleep sensors and/or biometric sensors for sensing sleep of a person and/or biometrics of a person. E.g., the sensor may be and/or include a heart rate sensor, a brain activity sensor, a breath and/or lung output sensor, a snoring sensor, a skin temperature sensor, a perspiration sensor, etc. Even further, the system 100 and/or specifically the monitor 195 may include an accelerometer for sensing acceleration and/or movement of the system 100 e.g. for use in accordance with present principles (e.g. the accelerometer may detect movement of a person while supposedly sleeping and/or data therefrom may be used to determine whether a user is actually sleeping based on the amount of movement).

Additionally, though now shown for clarity, in some embodiments the system 100 may include a gyroscope for e.g. sensing and/or measuring the orientation of the system 100, as well as an audio receiver/microphone in communication with the processor 122 and providing input thereto based on e.g. a user providing audible input to the microphone. Still further, and also not shown for clarity, the system 100 may include a GPS transceiver that is configured to e.g. receive geographic position information from at least one satellite and provide the information to the processor 122. However, it is to be understood that another suitable position receiver other than a GPS receiver may be used in accordance with present principles to e.g. determine the location of the system 100.

Figure 2:
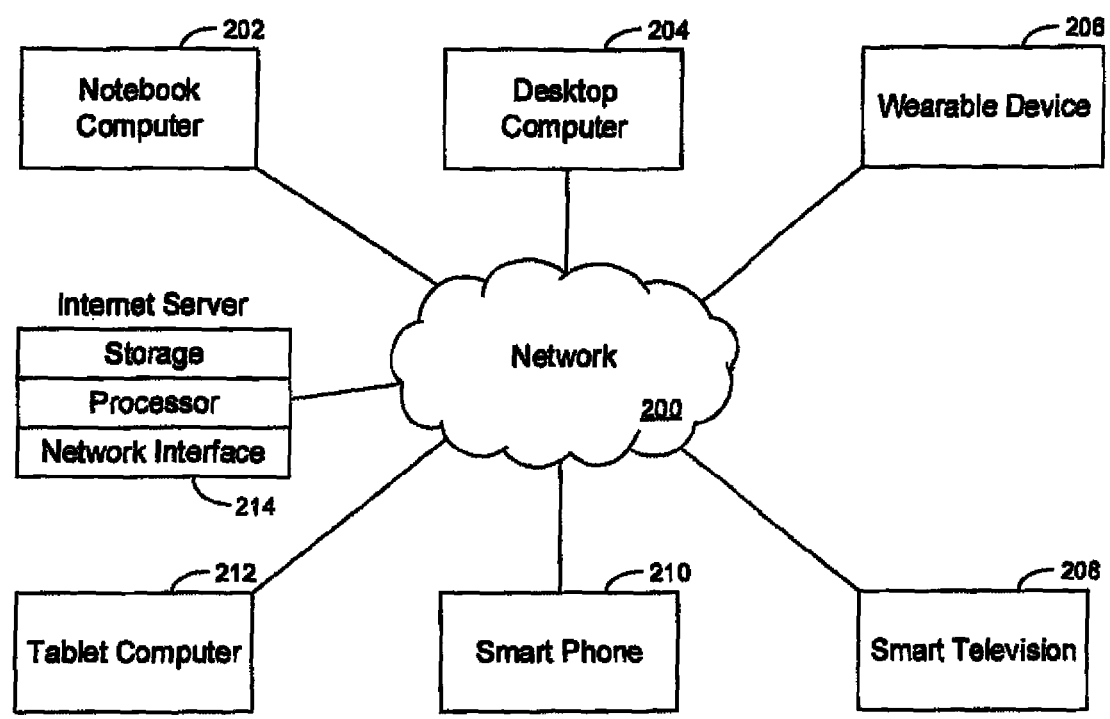
FIG. 2 is a block diagram of a network of devices in accordance with present principles.

Before moving on to FIG. 2, it is to be understood that an example client device or other machine/computer may include fewer or more features than shown on the system 100 of FIG. 1. In any case, it is to be understood at least based on the foregoing that the system 100 is configured to undertake present principles.

Turning now to FIG. 2, it shows example devices communicating over a network 200 such as e.g. the Internet in accordance with present principles. It is to be understood that e.g. each of the devices described in reference to FIG. 2 may include at least some of the features, components, and/or elements of the system 100 described above. In any case, FIG. 2 shows a notebook computer 202, a desktop computer 204, a wearable device 206 (such as e.g. a smart watch, a smart bracelet, a fitness monitoring device, a biometric monitoring device, a sleep monitoring device, etc.), a smart television (TV) 208, a smart phone 210, a tablet computer 212, and a server 214 in accordance with present principles such as e.g. an Internet server that may e.g. provide cloud storage accessible to the devices 202-212. It is to be understood that the devices 202-214 are configured to communicate with each other over the network 200 to undertake present principles.

Figure 3:
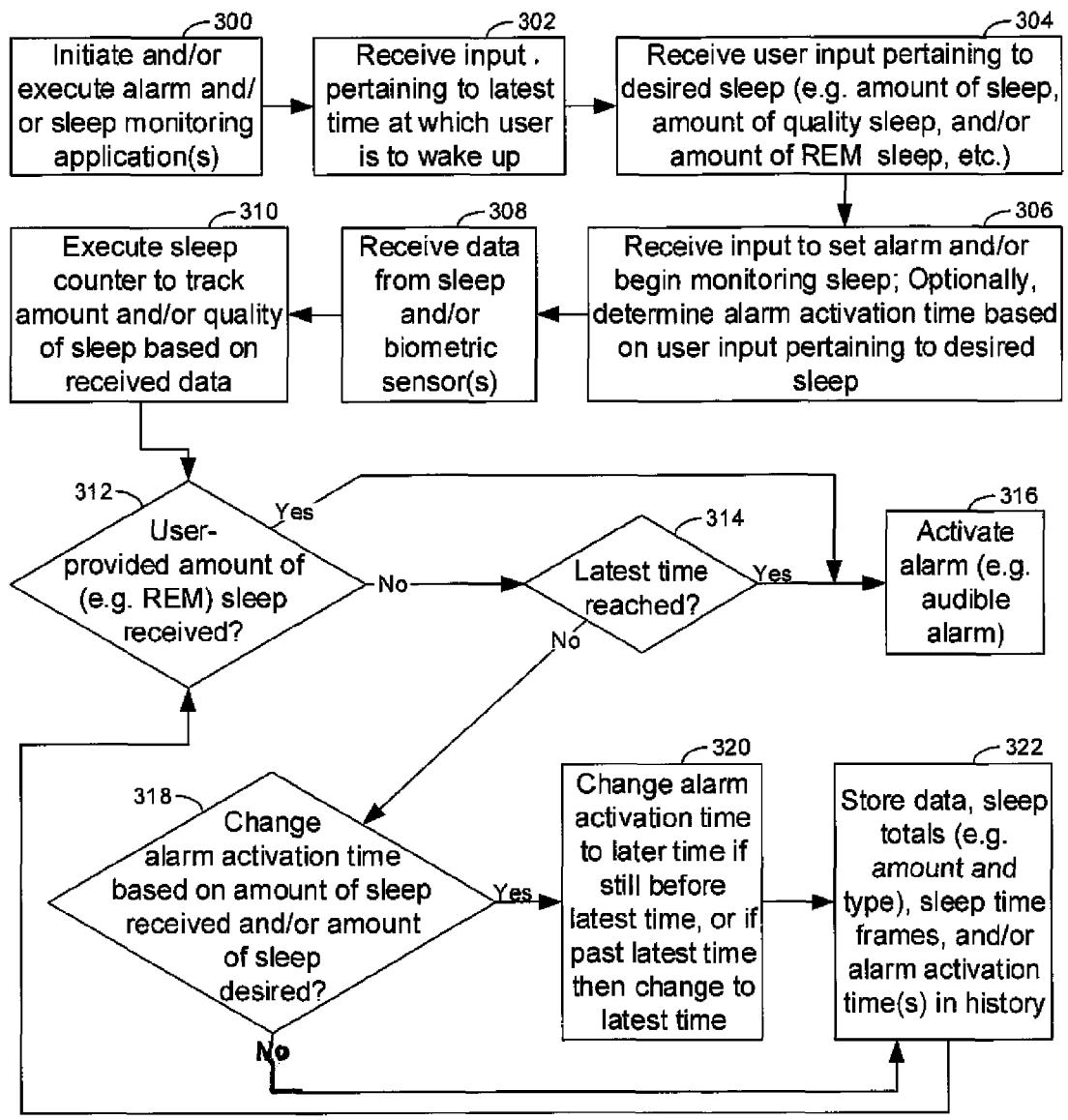
FIGS. 3 and 4 are flow charts showing example algorithms in accordance with present principles.

Referring to FIG. 3, it shows example logic that may be undertaken by a device such as the system 100 in accordance with present principles. Beginning at block 300, the logic initiates and/or executes one or more applications for undertaking present principles, such as e.g. an alarm application and/or a sleep monitoring application. Note that in some embodiments the alarm application and sleep monitoring application may in fact be a single application for providing alarms and monitoring sleep. In any case, upon initiation and/or execution of the application(s), the logic proceeds from block 300 to block 302. At block 302 the logic receives input to the device undertaking the present logic (referred to below as the "present device") pertaining to a latest time (e.g. threshold time) at which the user desires to wake up based on an alarm activated using the application.

After block 302 the logic proceeds to block 304 where the logic receives user input pertaining to sleep goals and/or the sleep the user desires to receive during a period of time (e.g. that night, within a twenty four hour period, within a twelve hour period, etc.) prior to activation of the alarm, such as e.g. a total amount and/or duration of sleep, a total amount of quality sleep (e.g. deep sleep), and/or a total amount of rapid eye movement (REM) sleep). The logic thereafter moves to block 306 where the logic receives user input for the device to set the alarm and/or begin monitoring the user's sleep (e.g. based on data from sleep and/or biometric sensors). Also at block 306, the logic may determine, identify, and/or estimate (e.g. based on a sleep history as discussed further below) an alarm activation time that may be e.g. before the latest time input by the user but still at which the user may have achieved one or more sleep desires and/or sleep goals e.g. as input at block 304.

After block 306, the logic proceeds to block 308 at which the logic receives data from sleep and/or biometric sensors monitoring sleep and/or biometrics of the user (e.g. such as a may be located on a biometric "smart" bracelet worn by the user, where such a bracelet may in fact be the present device or another device in communication with the present device). Then at block 310 the logic initiates and/or executes a sleep counter (e.g. a timer embodied in software) to track and/or count, based on the data being received, the types and/or classes of sleep per the user input received at block 304, such as e.g. the total amount and/or duration of sleep, the total amount of quality (e.g. deep) sleep, and/or the total amount of REM sleep.

The logic then proceeds to decision diamond 312 where the logic determines whether a user provided total amount and/or duration of sleep, total amount of quality sleep, and/or total amount of REM sleep has been achieved (e.g. based on the data received at block 308 and/or as tracked by the counter at block 310). Upon an affirmative determination at diamond 312, the logic proceeds to block 316, which will be described shortly. However, upon a negative determination at diamond 312, the logic instead moves to decision diamond 314. At diamond 314, the logic determines whether, e.g. regardless of whether one or more user-desired parameters have been met such as the total amount of sleep or total amount of REM sleep, the latest time specified by the user at block 302 has been reached.

An affirmative determination at diamond 314 causes the logic to move to block 316, where the logic activates one or more alarms, such as e.g. an audible alarm, an alarm presented on a display of the present device (e.g. a blinking alert), and/or a vibration alarm e.g. based on actuation of a vibrating element such as the element 193 described above. However, if instead at diamond 314 a negative determination is made, the logic moves to decision diamond 318 where the logic determines whether to change an alarm activation time, such as e.g. the one determined at block 306, based on one or more amounts of sleep actually received by the user as determined by the present device based on sleep and/or biometric data it has received, and/or based on e.g. a determination and/or estimation of how much more time may be needed beyond the alarm actuation time for the user to reach one or more desired amounts of sleep (e.g. based on one or more current sleep patterns and/or sleep interruptions).

A negative determination at diamond 318 causes the logic to proceed to block 322, which will be described shortly. However, an affirmative determination at diamond 318 instead causes the logic to proceed to block 320, at which the logic may change the alarm activation time to either a later time that is still before the latest time specified by the user at block 302 or the latest time if the change to the alarm activation time would result in an activation of the alarm after the latest time. After block 320 the logic proceeds to block 322, at which the logic may store in a history (e.g. database and/or data table) data it has received such as e.g. the sleep and/or biometric data described above, as well as one or more sleep totals, sleep time frames and/or specific periods (e.g. times of day) at which the user slept, alarm activation times, and/or so-called "latest times" (e.g. threshold times) at which the user desires to wake up regardless of reaching one or more desired parameters pertaining to the user's sleep. After block 322, the logic may revert back to decision diamond 312 and proceed therefrom.

Figures 4, 5:
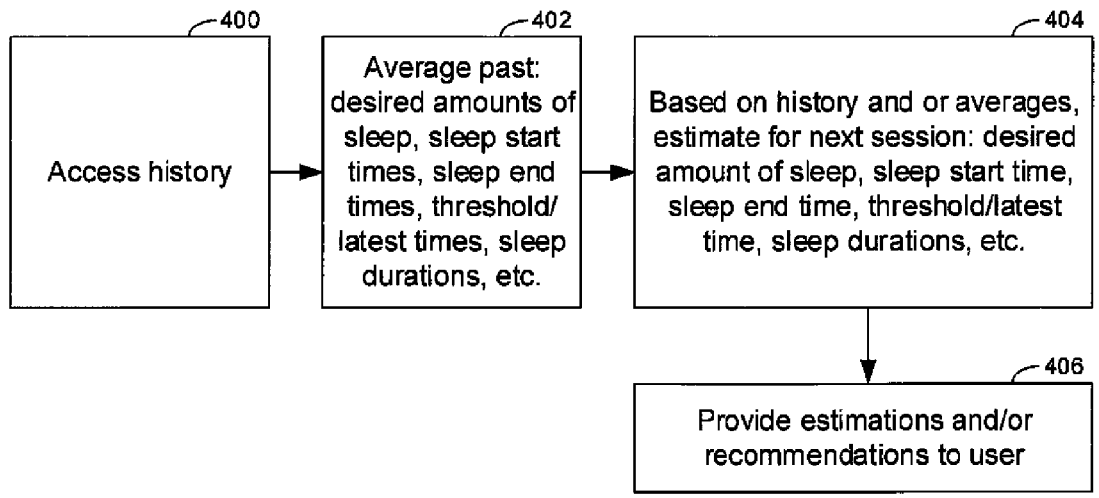
FIG. 5 is an example data table in accordance with present principles.

Continuing the detailed description now in reference to FIG. 4, it shows logic that may also be undertaken by a device such as the system 100 in accordance with present principles. Furthermore, it is to be understood that the logic of FIG. 4 may in some embodiments be executed in conjunction with the logic of FIG. 3, and/or may be separately executed. In any case, the logic of FIG. 4 begins at block 400, where the logic accesses a history (e.g. database and/or data table) of data pertaining to a user's past sleep sessions such as the sleep and/or biometric data described above, as well as one or more sleep totals, sleep time frames and/or specific periods (e.g. times of day) at which the user slept, alarm activation times, and/or latest times at which the user desires to wake up regardless of reaching one or more desired parameters pertaining to the user's sleep.

Note that the logic may access the history at block 400 e.g. in response to a user request to observe such data pertaining to previous sleep sessions, and/or to make a determination and/or estimation of an appropriate alarm activation time based on past data and e.g. currently desired user parameters such as may occur at e.g. at block 306 described above.

Regardless, after block 400 the logic moves to block 402 where the logic may compute and/or identify an average (and/or median and/or mode) of one or more classes and/or types of data such as e.g. one or more sleep totals and/or amounts, sleep time frames and/or specific durations (e.g. times of day, start times, end times, uninterrupted sleep durations, etc.) at which the user slept, alarm activation times, latest times specified by a user, etc. Thereafter, the logic moves to block 404 where the logic may, based on the history and/or the averages, medians, and/or modes determined and/or computer at block 402, determine e.g. most likely figures, time frames, numbers, etc. for one or more of the classes and types of data for a next sleep session of the user. The logic then proceeds to block 406 where the logic may provide the determinations and/or estimations from block 404 to the user by e.g. presenting them on a display of the device undertaking the logic of FIG. 4.

Before describing FIG. 5, it is to be understood in reference to block 402 that the averages, medians, and/or modes determined thereat maybe based on a (e.g. user-specified) threshold or maximum amount or most recent number of previous sleep sessions in the history, such as e.g. a most-recent week, month, and/or year.

Now in reference to FIG. 5, it shows an example data table 500 that may form at least a portion of a history that is accessed in accordance with present principles, such as e.g. at block 400 as described above. As may be appreciated from the table 500, the rows of the table 500 pertain to respective sleep sessions, while the columns of the table 500 pertain to various parameters and/or types of data. Thus, upon determining and/or identifying data based on input from a sleep sensor, a device undertaking present principles may create and/or add such data as an entry to the table 500.

Describing the columns of the table 500, first note that the respective parameters and/or data types for columns shown are examples, and that any of the parameters and/or data types discussed herein may be included in respective columns of a data table such as the table 500. In any case, a first column 502 includes entries for latest and/or threshold alarm activation times as e.g. specified by a user, a column 504 includes entries for amounts of sleep desired by a user, a column 506 includes entries for amounts of REM sleep desired by the user, a column 508 includes entries for sleep start times (e.g. times of day), a column 510 includes entries for sleep end times (e.g. times of day), a column 512 contains entries for amounts of sleep received for respective sleep sessions, and a column 514 contains entries for amounts of REM sleep received for respective sleep sessions.

Figure 6:
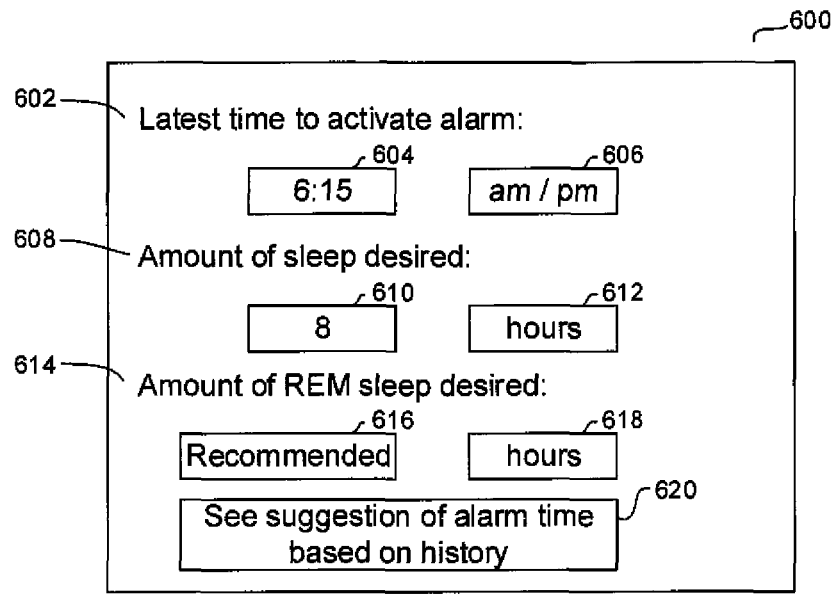
FIGS. 6-8 are example user interfaces (UI) in accordance with present principles.

Before moving on to the description of FIG. 6, it is to be understood that separate histories such as the data table 500 described above may be associated with and for e.g. different users, user profiles, and/or devices (e.g. sleep monitoring devices and/or wearables in communication with and/or forming a part of a device such as the system 100), and thus more than one history may be stored at the device. Nonetheless, it is to also be understood that a history may be associated with plural users, user profiles, and/or devices, where it may contain separate sections for each respective user, user profile, and/or device, and/or may not separate sections and build and/or add to the history rows of data based on chronological order or reverse-chronological order.

Now in reference to FIG. 6, it shows an example user interface (UI) 600 presentable on a device such as the system 100 in accordance with present principles. It is to be understood that the UI 600 may be for a user to provide input regarding one or more user-defined parameters for a sleep session, and thus the UI 600 may be presented as part of a sleep monitoring and/or alarm application for undertaking present principles, and/or may be presented upon user input such as invocation of a selector element and/or icon associated with such an application.

In any case, the UI 600 includes a first area 602 pertaining to a latest and/or threshold time to activate an alarm e.g. regardless of one or more user-specified desired amounts of sleep. Thus, the area 602 includes an entry box 604 at which a user may enter (e.g. using an on-screen keyboard) and/or otherwise provide input specifying the threshold and/or latest time. The area 602 also includes a selector element 606 that is selectable to e.g. cause a drop-down and/or overlay menu to be presented containing two selectable options for the time entered to box 604 to pertain to either an a.m. time or a p.m. time (e.g. if the time entered to box 604 was not entered as a military time).

The UI 600 also includes a second area 608 pertaining to a user-specified desired amount of sleep. The area 608 includes an entry box 610 at which a user may enter (e.g. using an on-screen keyboard) and/or otherwise provide input specifying the amount. The area 608 also includes a selector element 612 that is selectable to e.g. cause a drop-down and/or overlay menu to be presented containing one or more selectable options for units of time to be associated with a number entered to box 610, such as e.g. hours, minutes, and seconds.

Still further, the UI 600 includes a third area 614 pertaining to a user-specified desired amount of REM sleep specifically. The area 616 includes an entry box 616 at which a user may enter (e.g. using an on-screen keyboard) and/or otherwise provide input specifying the REM amount. The area 614 also includes a selector element 618 that is selectable to e.g. cause a drop-down and/or overlay menu to be presented containing one or more selectable options for units of time to be associated with a number entered to box 616, such as e.g. hours, minutes, and seconds.

However, note that as shown in the example of FIG. 6, the box 616 contains input that the user wishes to receive a "recommended" amount of REM sleep rather than a specific user-specified amount. E.g., a sleep monitoring application presenting the UI 600 may include instructions and/or data for recommended amounts of REM sleep e.g. based on recommendations from the United States Surgeon General and/or another medical authority, based on previous sleep sessions and associated user-provided desired amounts, based on the amount of total sleep desired as entered to box 610, etc. Such recommendation data may be accessible to the device e.g. over the Internet, and/or stored at the device. In any case, a recommended amount may be used in accordance with present principles when a user desires to receive such a "recommended" amount rather than providing a specific number. Note that the user may enter the word "recommended," and/or such an option may be selected e.g. based on selection of a selector element and/or from a drop down and/or overlay box presented when the box 616 is selected and/or invoked for entry of input thereto.

Also, note that even though not shown in FIG. 6, in some embodiments when the "recommended" option is selected, a number associated with the recommendation may be presented along with the word "recommended." Thus, e.g., if the U.S. Surgeon General's recommendation were for 1.6 hours of REM sleep for an eight hour sleep session, 1.6 hours may be indicated adjacent to the word "recommended" in box 616. Even further, note that although the discussion above on recommended parameters pertaining to sleep was described in reference to REM sleep, similar recommendations may be invoked by a user and/or used in accordance with present principles for any of the other parameters, types of data (e.g. sleep times, durations, deep sleep amounts), etc. discussed herein.

Still further, although only a few areas pertaining to sleep metrics, parameters, and/or amounts are shown, it is to be understood that the UI 600 may include still others for e.g. any of the metrics, parameters, user-desired amounts, etc. discussed herein.

Still in reference to FIG. 6, the UI 600 may also include a selector element 620. The element 620 is selectable to automatically without further user input responsive thereto present one or more suggestions to a user, such as may be provided at block 406 of FIG. 4 discussed above. Thus, e.g., responsive to selection of the selector element 620, a UI such as the UI 700 of FIG. 7 may be presented.

Figure 7:
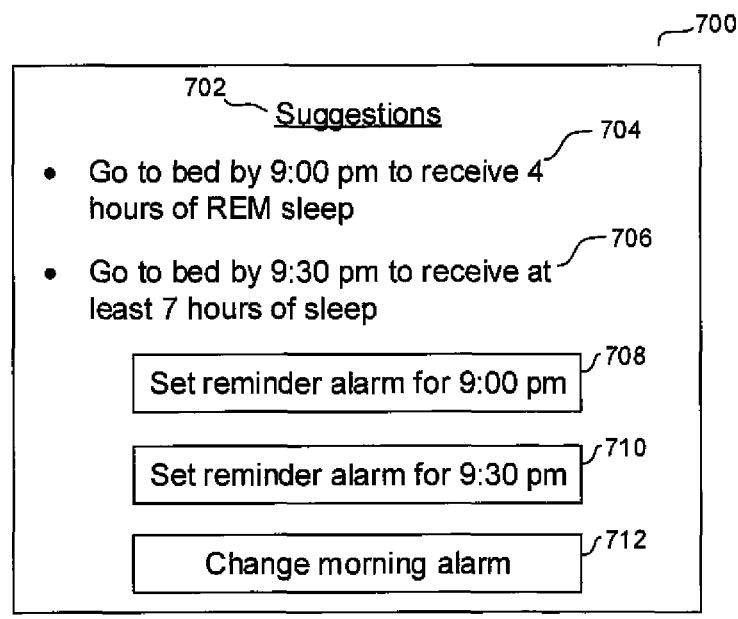

Accordingly, describing the UI 700 of FIG. 7, it includes an indication 702 that the UI 700 pertains to suggestions regarding sleep to be received by a user. The UI 700 also includes a first suggestion 704 indicating that (e.g. based on a history that was accessed in accordance with present principles) the user should go to sleep by 9:00 p.m. to receive four hours of REM and/or deep sleep. The UI 700 also includes a second suggestion 706 indicating that the user should go to sleep by 9:30 p.m. to receive at least seven hours of sleep e.g. based on previous sleep disruptions e.g. in the middle of a previous night as derived from the history. Though not shown, the UI 700 may include still other suggestions such as e.g. a time at which an alarm is to occur for a user to cease a sleep session while still conforming with e.g. a desired amount of REM sleep. As another example, e.g. a suggestion may be to go to sleep at a time e.g. half an hour earlier than an average sleep start time in order to achieve a common and/or average sleep goal as provided by the user for previous sleep sessions.

The UI 700 may also include other features, such as e.g. a first selector element 708 selectable to automatically without further user input responsive thereto configure the device and/or sleep monitoring/alarm application to set a "reminder" alarm for 9:00 p.m. e.g. so that the user may be reminded to conform with the first suggestion 704. A second selector element 710 is also shown that is selectable to automatically without further user input responsive thereto configure the device and/or sleep monitoring/alarm application to set a "reminder" alarm for 9:30 p.m. e.g. so that the user may be reminded to conform with the second suggestion 706. Also note that yet a third selector element 712 is shown that is selectable to automatically without further user input responsive thereto configure the device and/or sleep monitoring/alarm application to e.g. present another UI from which the user may establish and/or change a threshold and/or latest time at which an alarm is to occur, and/or to change still other alarms and/or user-specified parameters. For example, in some embodiments selection of the element 712 may automatically cause the device to present the UI 600 described above.

Figure 8:
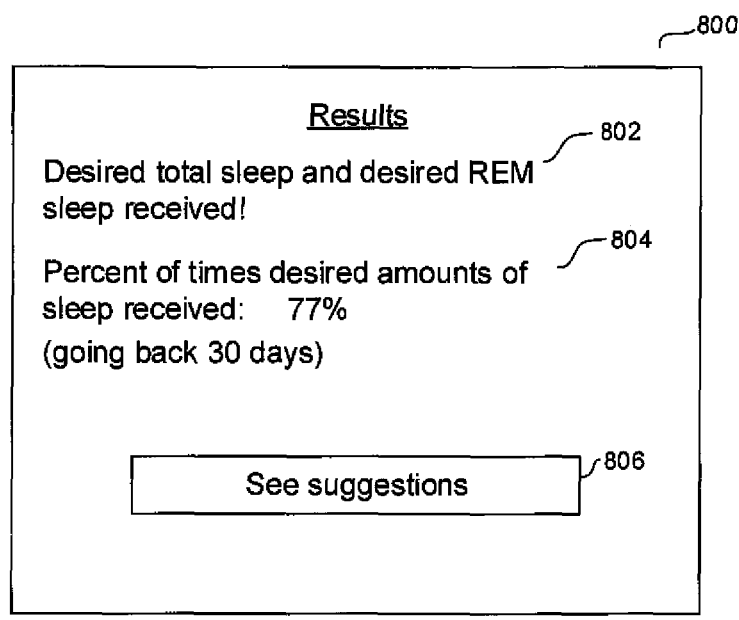

Before moving on to the description of FIG. 8, also note that still other suggestions may be made and/or presented on the UI 700, such as for any of the other parameters, data, types of sleep, etc. as discussed herein.

Now in reference to FIG. 8, it shows an example UI 800 showing sleeps results for a user after a sleep session (e.g. night of sleep), and whether one or more parameters and/or user-desired amounts of sleep have been achieved. The UI 800 thus includes at least one result 802 indicating in the present example that e.g. both a desired total amount of sleep and a desired amount of REM sleep have been achieved. The UI 800 may also include statistics on the user's sleep and/or sleep data, such as may be included in an indication 804, which indicates that e.g. for the past thirty days and/or sleep sessions, the user has received their desired amount(s) of sleep seventy seven percent of the time (e.g. in seventy seven percent of sleep sessions).

The UI 800 also includes a selector element 806 selectable to automatically without further user input responsive thereto configure the device to present suggestions on the device for e.g. conforming with one or user-input parameters for sleep. Thus, e.g., in some embodiments the UI 700 may be presented responsive to selection of the element 806.

It may now be appreciated that present principles provide for, based on monitoring a user's R.E.M. sleep, a device to have one or more settings such that if a user receives e.g. eight hours of total sleep, and/or a correct (e.g. desired) amount of deep sleep, then an alarm may be activated to wake the user up. However, should the user need to get up at a certain time no matter what such as e.g. for work or a meeting, present principles provide for such a setting to accordingly activate the alarm regardless of sleep amounts and/or sleep durations.

Thus, e.g., if a user goes to bed by 10:00 p.m., if the user were to receive eight good hours (or a set, e.g. user-specified amount) of sleep, their device may wake them up at 6:00 a.m. even if that is before the latest time at which the user has indicated they need to wake up. However if e.g. a smoke alarm started with its low battery beep feature at 2:00 a.m. and woke the user up unexpectedly at that time, then the user's device may compensate for whatever the lack of sleep was until the user got back to sleep after adjusting the smoke alarm to wake them up at e.g. 6:30 a.m. (thus, the device has determined the user was awake for half an hour from 2:00 a.m. to 2:30 a.m.). However, in this example the user may have also indicated that, no matter what, their alarm is to be activated by 7:00 a.m. in order to not be late for work.

It may also be appreciated that present principles may e.g. help individuals suffering from depression that can be exacerbated by constant and/or habitual oversleeping, which in turn can further exacerbate their mental health. Suggestions may thus be provided in accordance with present principles for them to get the correct amount of sleep they need. Thus, in one aspect a device undertaking present principles may be used as an indicator for such a user to get out of bed at the right time.

Before concluding, it is to be understood that although e.g. a software application for undertaking present principles may be vended with a device such as the system 100, present principles apply in instances where such an application is e.g. downloaded from a server to a device over a network such as the Internet. Furthermore, present principles apply in instances where e.g. such an application is included on a computer readable storage medium that is being vended and/or provided, where the computer readable storage medium is not a carrier wave and/or a signal per se.

While the particular DETERMINING WHETHER TO CHANGE A TIME AT WHICH AN ALARM IS TO OCCUR BASED AT LEAST IN PART ON SLEEP DATA is herein shown and described in detail, it is to be understood that the subject matter which is encompassed by the present application is limited only by the claims.

What is claimed is:

1. A device, comprising:
   a processor; and
   storage accessible to the processor and bearing instructions executable by the processor to:
   receive data from a sleep sensor in communication with the device;
   based at least in part on the data, determine whether to change a first time at which an alarm is to occur at the device, wherein the determination whether to change the first time is based at least in part on a first amount of sleep a person is to receive and is based at least in part on a threshold time at which the alarm is to occur regardless of the first amount of sleep;
   in response to a determination that the threshold time has not been reached and that the first amount of sleep has not been reached, determine a second time at which the alarm is to occur for the first amount of sleep to be reached, wherein the determination of the second time is at least in part based on an estimation that is based on the data that is received of when the first amount of sleep will be reached;
   in response to a determination that the second time is past the threshold time, set the alarm to occur at the threshold time; and
   in response to a determination that the second time is before the threshold time, set the alarm to occur at the second time.

2. The device of claim 1, wherein the data from the sleep sensor pertains to rapid eye movement (REM) sleep.

3. The device of claim 2, wherein the determination whether to change the first time at which the alarm is to occur at the device is based at least in part on an amount of REM sleep the person has received within a twenty four hour period comprising the time at which the determination is made.

4. The device of claim 3, wherein a counter at the device is used at least in part to determine, based on the data, the amount of REM sleep.

5. The device of claim 3, comprising a sleep monitor which monitors sleep, wherein the sleep monitor comprises the sleep sensor and provides the data to the processor of the device to determine the amount of REM sleep in response to receipt of input from the sleep sensor, wherein the sleep sensor contacts at least a portion of the person to monitor sleep of the person.

6. The device of claim 5, wherein the sleep monitor comprises a sleep monitoring application for tracking and storing amount of sleep and type of sleep.

7. The device of claim 1, wherein the first amount of sleep pertains to an amount of rapid eye movement (REM) sleep.

8. The device of claim 1, wherein the instructions are further executable to:
   in response to a determination that the threshold time has been reached, provide the alarm.

9. The device of claim 1, wherein the instructions are further executable to:
   in response to a determination that the first amount of sleep has been reached, provide the alarm.

10. The device of claim 1, wherein the instructions are further executable to:
    access a history of data pertaining to sleep; and
    based at least in part on the history of data, provide a suggestion at the device of a time at which an alarm is to occur.

11. A method, comprising:
    receiving input at an information handling system pertaining to an amount of sleep of a first type to receive prior to activating an alarm;
    receiving input at the information handling device pertaining to a threshold time at which the alarm is to be activated regardless of the amount of sleep;
    monitoring a user's sleep based on data from a sensor;
    determining whether at least one of the amount of sleep has been reached and the threshold time has been reached;
    in response to determining that the threshold time has not been reached and that the amount of sleep has not been reached, determining a second time at which an alarm is to occur for the amount of sleep to be reached, wherein the determination of the second time is at least in part based on an estimation, based on data that is received, of when the amount of sleep will be reached;

in response to determining that the second time is past the threshold time, setting the alarm to occur at the threshold time; and in response to determining that the second time is before the threshold time, setting the alarm to occur at the second time.

12. The method of claim 11, further comprising:

in response to determining that at least one of the amount of sleep has been reached and the threshold time has been reached, activating the alarm.

13. The method of claim 11, further comprising:

in response to determining that neither the amount of sleep has been reached nor the threshold time has been reached, declining to activate the alarm.

14. The method of claim 11, comprising:

presenting, via a user interface (UI) that is presented on a display accessible to the information handling device, an indication of a time at which the alarm is to occur based on the amount of sleep, wherein the indication is determined based at least in part on a history of data pertaining to sleep.

15. A computer readable storage medium (CRSM) that is not a transitory signal, the computer readable storage medium comprising instructions executable by a processor to:

receive input pertaining to an amount of sleep of a first type a person desires to receive prior to activation of an alarm;

monitor sleep of the person based on input from a sensor;

based at least in part on the input, and based at least in part on a threshold time and the amount of sleep of the first type the person desires to receive prior to activation of the alarm, determine a time at which the alarm is to occur;

in response to a determination that the threshold time has not been reached and that the amount of sleep has not been reached, determine a second time at which an alarm is to occur for the amount of sleep to be reached, wherein the determination of the second time is at least in part based on an estimation based on data indicating when the amount of sleep will be reached;

in response to a determination that the second time is past the threshold time, set the alarm to occur at the threshold time; and in response to a determination that the second time is before the threshold time, set the alarm to occur at the second time.

16. The CRSM of claim 15, wherein the instructions are further executable to:

identify that the threshold time is a time at which the alarm is to occur regardless of whether the amount of sleep has been reached.

17. The CRSM of claim 15, wherein the instructions are further executable to:

audibly provide the alarm, at least in part using a speaker, at the time at which the alarm is to occur.

18. The CRSM of claim 15, wherein the amount of sleep is a desired amount of sleep, and wherein the instructions are executable by the processor to:

subsequent to activation of the alarm, present on a display data pertaining to an actual amount of sleep the person has received and whether the desired amount of sleep has been met.

19. The CRSM of claim 15, wherein the instructions are executable by the processor to:

present, via a user interface (UI) presented on a display accessible to the processor, a suggestion of a time to go to sleep that is based at least in part on the amount of sleep the person desires to receive prior to activation of the alarm;

wherein the amount of sleep is a first amount of sleep, wherein the first amount of sleep pertains to a total amount of sleep, wherein the suggestion is a first suggestion, and wherein the instructions are further executable to:

receive input pertaining to a second amount of sleep the person desires to receive prior to activation of the alarm, the second amount of sleep pertaining to rapid eye movement (REM) sleep;

present, via the UI, a second suggestion of a time to go to sleep that is based at least in part on the second amount of sleep.

20. The CRSM of claim 15, wherein the first type pertains to rapid eye movement (REM) sleep.

* * * * *